United States Patent [19]

Redding, Jr.

[11] Patent Number: 5,209,879

[45] Date of Patent: May 11, 1993

[54] METHOD FOR INDUCING TRANSFORMATIONS IN WAXES

[76] Inventor: Bruce K. Redding, Jr., 8514 Lyons Pl., Philadelphia, Pa. 19018

[21] Appl. No.: 505,849

[22] Filed: Apr. 6, 1990

[51] Int. Cl.$^5$ .................. B29B 13/08; B29K 91/00
[52] U.S. Cl. ............................... 264/23; 264/69; 264/272.12; 264/325; 264/330; 264/345; 106/270; 208/24; 204/157.62; 523/300; 425/174.2; 425/803
[58] Field of Search .............. 264/23, 330, 340, 345, 264/346, 22, 69, 70, 319, 322, 325, 272.12; 425/174, 803, 174.2; 204/157.15, 157.42, 157.62; 106/270, 271; 208/24; 523/300

[56] References Cited

U.S. PATENT DOCUMENTS

| | | | |
|---|---|---|---|
| 3,194,640 | 7/1965 | Nesh | 204/157.42 |
| 3,306,835 | 2/1967 | Magnus | 204/157.62 |
| 3,423,794 | 1/1969 | Wilson | 425/174.2 |
| 4,288,398 | 9/1981 | Lemelson | 264/23 |
| 4,311,571 | 1/1982 | Mack | 204/157.62 |
| 4,324,756 | 4/1982 | Kepes et al. | 264/322 |
| 4,446,087 | 5/1984 | Templin | 264/330 |
| 4,874,596 | 10/1989 | Lemelson | 204/157.15 |

FOREIGN PATENT DOCUMENTS 730574  4/1980  U.S.S.R. ............... 425/174.2

Primary Examiner—Jeffery Thurlow
Assistant Examiner—Mathieu Vargot
Attorney, Agent, or Firm—Robert S. Lipton

[57] ABSTRACT

The method and apparatus of this invention transforms naturally occurring or synthetic waxes into a state characterized by the fact that when the waxes solidify, they do so in forms different from those forms into which they would solidify except for the transformation. The transformation is achieved by subjecting the waxes to force. As examples of apparatuses which can supply the force to effect the transformation, a piston apparatus and an ultrasonic apparatus are disclosed. The triglyceride waxes are one type of wax which may be transformed by the method and apparatus of this invention. Transformed triglyceride waxes form superior shells when the waxes are used in an encapsulation process.

38 Claims, 12 Drawing Sheets

METHOD FOR INDUCING TRANSFORMATIONS IN WAXES

BACKGROUND OF THE INVENTION

Naturally occurring and synthetic waxes are extensively used in a wide cross-section of industries including the food preparation, pharmaceutical, cosmetic, and personal hygiene industries. The term wax is used to denote a broad class of organic ester and waxy compounds which span a variety of chemical structures and display a broad range of melting temperatures. Often the same compound may be referred to as either a "wax," "fat" or an "oil" depending on the ambient temperature. By whatever name it is called, the choice of a wax for a particular application is often determined by whether it is a liquid or solid at the temperature of the product with which it is to be used. Frequently it is necessary to extensively purify and chemically modify a wax to make it useful for a given purpose. Despite such efforts at modification, many physical characteristics of the waxes inherent in their structure still prevent them from being used successfully or demand that extensive additional treatments be undertaken.

For instance, extensive commercial use has been made of the naturally occurring carboxylic acids ("fatty acids") and their derivatives, most commonly the glyceryl derivatives in which all three hydroxy groups of the glyceryl molecule are esterified with a carboxylic acid. The carboxylic acids may be saturated or unsaturated. The tri-substituted glyceryls (triglycerides) are major components of most animal and plant fats/oils/waxes. When all three hydroxy groups of a glyceryl molecule have been esterified with the same fatty acid, it is referred to as a monoacid triglyceride. Whether one refers to triglycerides as "waxes," "fats," or "oils" depends upon the chain lengths of the esterified acids and their degree of saturation or unsaturation as well as the ambient temperature at which the characterization is made. Generally, the greater the degree of saturation and the longer the chain length of the esterified acids, the higher will be the melting point of the triglyceride.

An interesting feature of the triglycerides is that they may simultaneously solidify in more than one crystalline form within the same mass. This ability to exist in more than one crystalline state is termed "polymorphism" and is frequently observed among the waxes. Complicating the use of triglycerides even further is the fact that triglycerides exhibit a special form of polymorphism, designated monotropic polymorphism, in which the lower melting point crystal forms are unstable and convert over time to more stable forms, with the conversion dependent upon time and the temperature of the material. Monotropic polymorphism conversion always takes place in the direction towards the more stable crystal forms. Such conversion between polymorphic forms involves a structural rearrangement of the molecules.

For example, when melted, cooled, and solidified rapidly, the monoacid triglyceride glyceryl tristerate first hardens in a glass-like amorphous form which it then converts over time to a crystalline form (the alpha "α" form) having a hexagonal crystal lattice structure with a melting point of about 54° C. The polymorphic α form is only relatively stable. If heat is applied to α form material, the glyceryl tristerate will convert over time through an unstable intermediate form (the beta-prime "β'" form) to a yet higher melting point form (the beta "β" form), having a triclinic crystal lattice structure with a melting point of about 72° C. Once the conversion to the higher melting point β form is complete, the β form is stable. While many of the triglycerides, such as glyceryl tristerate, are available in relatively pure β form powders, these β forms are obtained from crystallization of the material from solvents into the powders. The powders themselves are usually not usable with processes which involve melting and resolidification since, once the triglyceride is melted and allowed to recrystallize, both the lower α and higher β melting point polymorphs are present in the resulting material.

Such polymorphism presents problems in the formulation of products using triglyceride waxes as well as in the stability of the products over time. The commercial use of the polymorphic materials often requires extensive treatment of the product to convert the triglycerides to the β form. If this is not done, the coexisting α and β forms will slowly rearrange over time within the product to convert the material in the α form to material in the β form. This rearrangement is both time and temperature dependent and may produce many undesirable features in the product. Thus, in preparation of such common foods as chocolates (to which triglycerides are added to affect the sense of taste), it is often necessary during processing to repeatedly cycle the temperature of the chocolate over a period of time to convert the residual c form triglycerides to β form. If the temperature is not cycled, the chocolate may well show undesirable crystallization characteristics.

This "tempering" is a common feature of processes where polymorphic waxes and, in particular, triglycerides are used. Such tempering procedures must also take into account the characteristics of the compounds with which the waxes are mixed, presenting a complex problem of how to treat the entire mixture.

Similar problems arise when waxes are used as coating materials in encapsulation processes. Often the wax coating fails to shield the coated material as intended. An examination of the physical structure of such wax coats indicates that fissures and cracks develop in the coating. Certainly for the polymorphic waxes, the transition between polymorphic forms (with the associated structural rearrangement of the molecules into different crystal structures) is inconsistent with the coating/encapsulation requirement that the coating material posses a stable structure over time. Further, wax coatings containing both polymorphic forms tend to lack physical strength and be poor moisture barriers. Although polymorphic waxes may eventually convert substantially to the stable higher melting point form as they age in a warm environment, this process can take a long time, leaving sensitive materials inadequately protected by such wax coating or shell layer. A coating made of such waxes provides little immediate protection for sensitive materials.

Nowhere in the prior art is it known how to treat waxes so that they solidify in a more stable state or, in the case of polymorphic waxes, in the stable β polymorphic form.

SUMMARY OF THE INVENTION

The method and apparatus of this invention transforms waxes which are in the liquid phase to a state from which the waxes solidify in a form having improved physical characteristics. For nonpolymorphic waxes, the transformation yields a form of the waxes which exhibits improved coating characteristics such as the ability to prevent access to the coated material by water or other environmental conditions. Similar improved coating characteristics are seen for the polymorphic waxes which, in addition, as a result of the transformation, solidify in the stable higher temperature polymorphic form. For the widely used polymorphic wax, glyceryl tristearate, the method and apparatus of this invention yield a molten form which solidifies in the stable β polymorph. The starting material for the method of this invention may be either a microcrystalline form of the wax, a liquid form, or a previously melted and resolidified form. The wax is melted, if necessary to obtain a liquid phase, and subjected in the liquid phase to force. For instance, the liquid wax may be placed in a chamber attached to a piston and subjected to the force of the stroke cycles of the piston. As an example of another means for applying force, the liquid wax may be exposed to ultrasound delivered by an ultrasonic transducer immersed in the liquid wax. The liquid transformed wax resulting from subjecting the wax to force exhibits improved physical characteristics and is particularly useful in encapsulating materials without the use of solvents.

It is an object of this invention to provide a method for the transformation of naturally occurring and synthetic waxes which alters the physical state of the waxes to improve their characteristics.

It is an object of this invention to provide a process whereby polymorphic waxes may be transformed in the liquid phase to produce a liquid form of the wax which solidifies in the stable higher melting point polymorphic form.

An additional object of this invention to provide a process for transforming liquid waxes so that such waxes may be used in encapsulation processes as superior shell materials.

A further object of this invention is to provide a piston apparatus suitable for transforming waxes to a more stable state.

Another object of this invention is to provide an ultrasonic apparatus suitable for transforming waxes to a more stable state.

Other useful objects of the invention will become apparent to those skilled in the art from the disclosure which follows.

DETAILED DESCRIPTION OF THE INVENTION

The term "wax" as used in this application is intended to have as broad a meaning as possible and contemplates organic ester and waxy compounds derived from animals, vegetables, and minerals including modifications of such compounds from all three sources in addition to those materials having similar properties which are synthesized. Examples of some of the naturally occurring and synthetic waxes which may be used either alone or in combination with the method and apparatus of this invention are shown below in Table 1.

TABLE 1

| | |
|---|---|
| GLYCERYL TRISTEARATE | GLYCERYL DISTEARATE |
| DYNASAN ™ 110, 114, 116, 118 | STEROTEX ™ HM, K |
| | COTTON FLAKES |
| CANOLA WAX/OIL | CASTOR WAX |
| SOYA FLAKES | BEESWAX |
| RAPESEED WAX | CANDELILLA WAX |
| CARNAUBA WAX | BOLER ™ WAX 1014 |
| MICROWAX | BE SQUARE ™ WAX #195A |
| (PETROLEUM BASED) | ENERGYBOOSTER ™ |
| SPECIAL FAT ™ 42, 44, 168 T | ASTOR ™ WAX 150 |
| BE SQUARE ™ WAX #195W | |
| ASTOR ™ WAX 180 | |

For purposes of disclosure in this application of the method and apparatus of this invention, it is convenient to consider and demonstrate the method and apparatus by their application to a class of commonly used waxes, the triglycerides.

In nature, triglycerides are usually found in association in complex mixtures. Depending upon the source of the triglyceride, whether animal or plant, the triglyceride may be formed from shorter or longer carboxylic acids which may in turn be either saturated or unsaturated. Triglycerides formed from shorter chain, unsaturated carboxylic acids, as a rule, melt at a lower temperature than triglycerides formed from longer-chain, saturated acids. In most cases, triglycerides are formed of more than one type of carboxylic acid. Further, the physical characteristics of a triglyceride (such as whether it exists as a liquid or solid at room temperature) are determined not only by which carboxylic acids were incorporated by esterification but also in which of the glyceryl hydroxy positions a given carboxylic acid was incorporated. Thus, animal triglycerides differ from plant triglycerides not so much in the overall ratios of saturated to unsaturated acids or of acids of given lengths, but rather in which of the three hydroxy positions in the glyceryl molecule unsaturated acids are to be found. Also, typically, naturally occurring triglyceride waxes which are solid at room temperature do not display a single sharp melting point because of the wide range of triglycerides present in most natural products.

Figure 1:
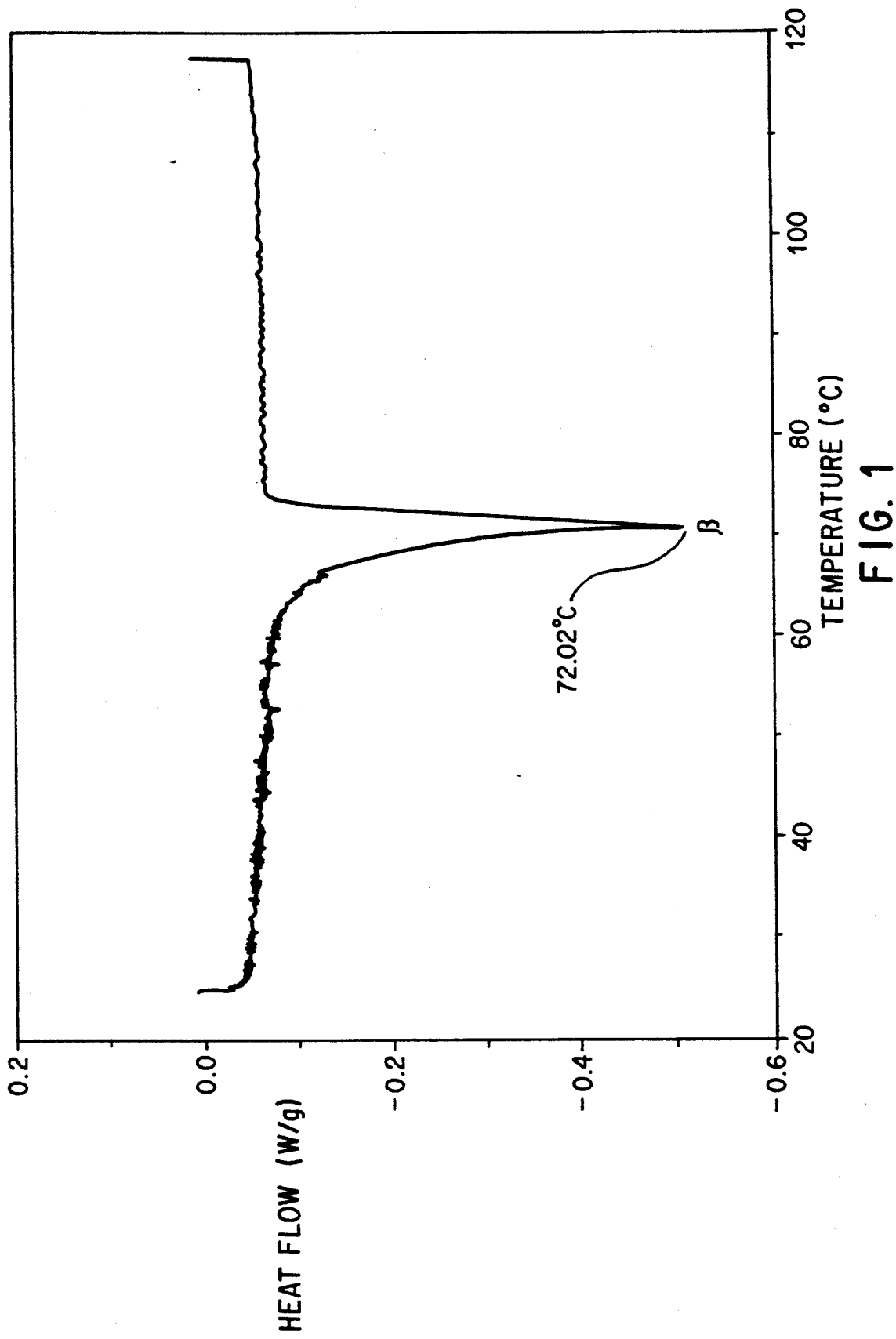
FIG. 1 is a differential scanning calorimeter (DSC) spectrum showing the endothermic melting point peak of the stable β polymorph of crystallized glyceryl tristerate (Dynasan 118) as provided by the manufacturer.

Triglyceride waxes may be obtained commercially with a choice of chain length of the carboxylic acids which form the triglycerides, as well as a choice of purity grades. Commercial preparations of triglycerides start with natural products in which a number of different triglycerides are associated with each other. Processing not only saturates the acid substituents but reduces the variety of triglycerides in the final material. The method and apparatus of this invention may be clearly demonstrated using the monoacid triglyceride, glyceryl tristerate ("tristearin") formed by the esterification of 18-carbon stearic acids with all three hydroxy groups of glyceryl. Stearic acid is a fully saturated carboxylic acid. The most suitable commercial grade of tristearin of which Applicant is aware is a product having the trademark "Dynasan 118" which is manufactured by Dynamit Nobel, a subsidiary of Huls America. Dynasan 118 is a highly purified material from a vegetable source which contains relatively few triglyceride molecules which have esterified acids of different lengths. Similar, although somewhat less pure triglyceride materials are also commercially available under the trademark Sterotex. As it is supplied by the manufacturer, Dynasan 118 is a white microcrystalline powder crystallized in the $\beta$ form as can be seen by the differential scanning calorimeter (DSC) spectrum of a sample of Dynasan 118 shown in FIG. 1. The presence of only a single endothermic peak centered at approximately 72° C. indicates that only a single polymorphic form is present with a melting point within the melting point temperature range of the $\beta$ form.

Figure 2:
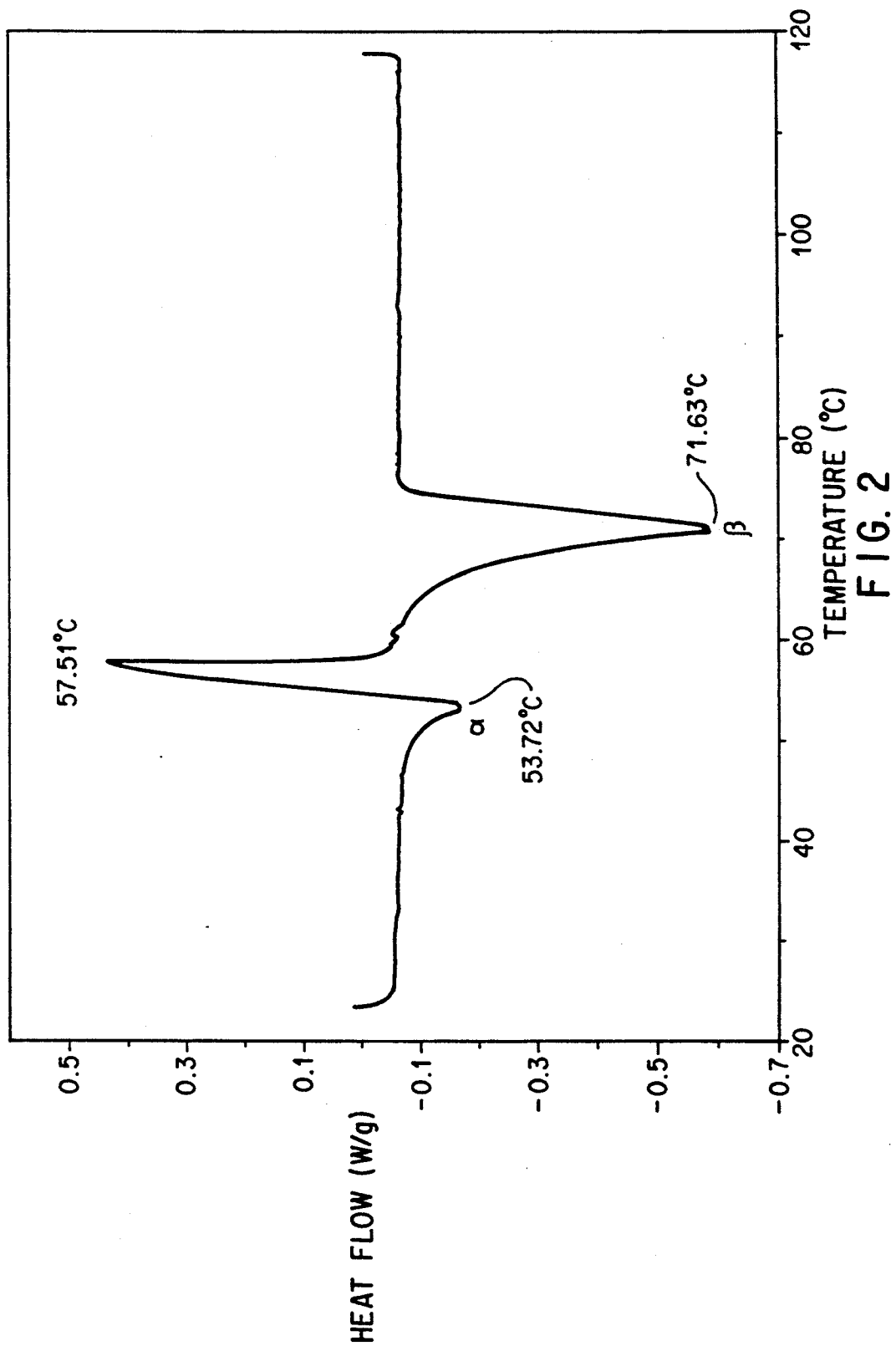
FIG. 2 is a DSC spectrum of glyceryl tristerate which has been melted and re-solidified showing the endothermic peaks corresponding to the α and β forms and the exothermic heat of crystallization.

Like other triglycerides, when the Dynasan 118 tristearin is heated to a molten phase and allowed to cool, it crystallizes in both the $\alpha$ and $\beta$ polymorphic forms as can be seen in FIG. 2 where the Dynasan 118 was first heated to 125° C. and then resolidified. The polymorphic $\alpha$ form melts at a lower temperature and is seen in the DSC spectrum of FIG. 2 as an endothermic peak centered at approximately 54° C. The stable polymorphic $\beta$ form melts at a higher temperature and is seen in the DSC spectrum of FIG. 2 as the more prominent endothermic peak centered at approximately 72° C. The resolidified tristearin obviously has coexisting within it both crystal structures. The upward (exothermic) peak centered at approximately 57.5° C. between the endothermic peaks for the $\alpha$ and $\beta$ forms in the DSC spectrum of FIG. 2 is the exothermic heat of crystallization. This Figure shows the classic DSC spectrum of the heat of crystallization of tristearin.

A few comments are in order with respect to the DSC spectra presented in the figures. First, the absolute height (or depth) of the peaks in the DSC spectra are reflective only of the mass of the sample used to generate that spectrum. Thus, differences in the height (or depth) of a peak from one spectrum to another are not significant in terms of identifying the polymorphic forms in which the material exists. The different polymorphic forms are distinguished by the fact that they melt at different temperatures.

The relative proportions of the polymorphic $\alpha$ and $\beta$ forms which crystallize from melted tristearin will vary depending upon the heating and cooling regimen to which the tristearin sample has been subjected. However, FIG. 2 is representative of tristearin when it is melted and resolidified. It is obvious from the width of the peaks in the DSC spectra of FIGS. 1 and 2 that a range of melting points exist for both the $\alpha$ and $\beta$ forms. The exact reason for this is unclear.

Applicant is aware of two possible explanations for the width of the peaks. First, it is suggested that even in the solid (crystallized) state, some non-ordered or randomly ordered tristearin may be trapped within the crystalline structures, thereby locally altering the crystal structure and its melting point. The second explanation is that, because of the nature of the commercial preparation of the tristearin, a totally pure, homogeneous material has not been obtained. For instance, not all of the stearic acid moieties may have been totally saturated. It is also possible that some shorter or longer chain carboxylic acids may have participated in the esterification, whether saturated or not. The range of compounds therefore yields a range of melting points which is reflected not only in the width of the DSC peaks but also in the fact that different samples have slightly different/shifted principal melting points. Applicant believes this second explanation is most likely. Applicant has observed that tristearins from different manufacturers and/or derived from different starting materials exhibit varying peak widths as well as slightly shifted melting points of the polymorphic forms as measured by the DSC. However, there may also be other factors at work which are unknown to the Applicant.

The discovery which is the subject of this invention is that the application of force to liquid phase waxes transforms the waxes into a different liquid state characterized by the fact that, when the waxes solidify, they do so in forms different from those forms into which they would solidify except for the application of force. The transformed waxes exhibit altered characteristics which make them more usable for manufacturing processes including encapsulation processes. This discovery is clearly demonstrated with respect to glyceryl tristearate.

Figure 3:
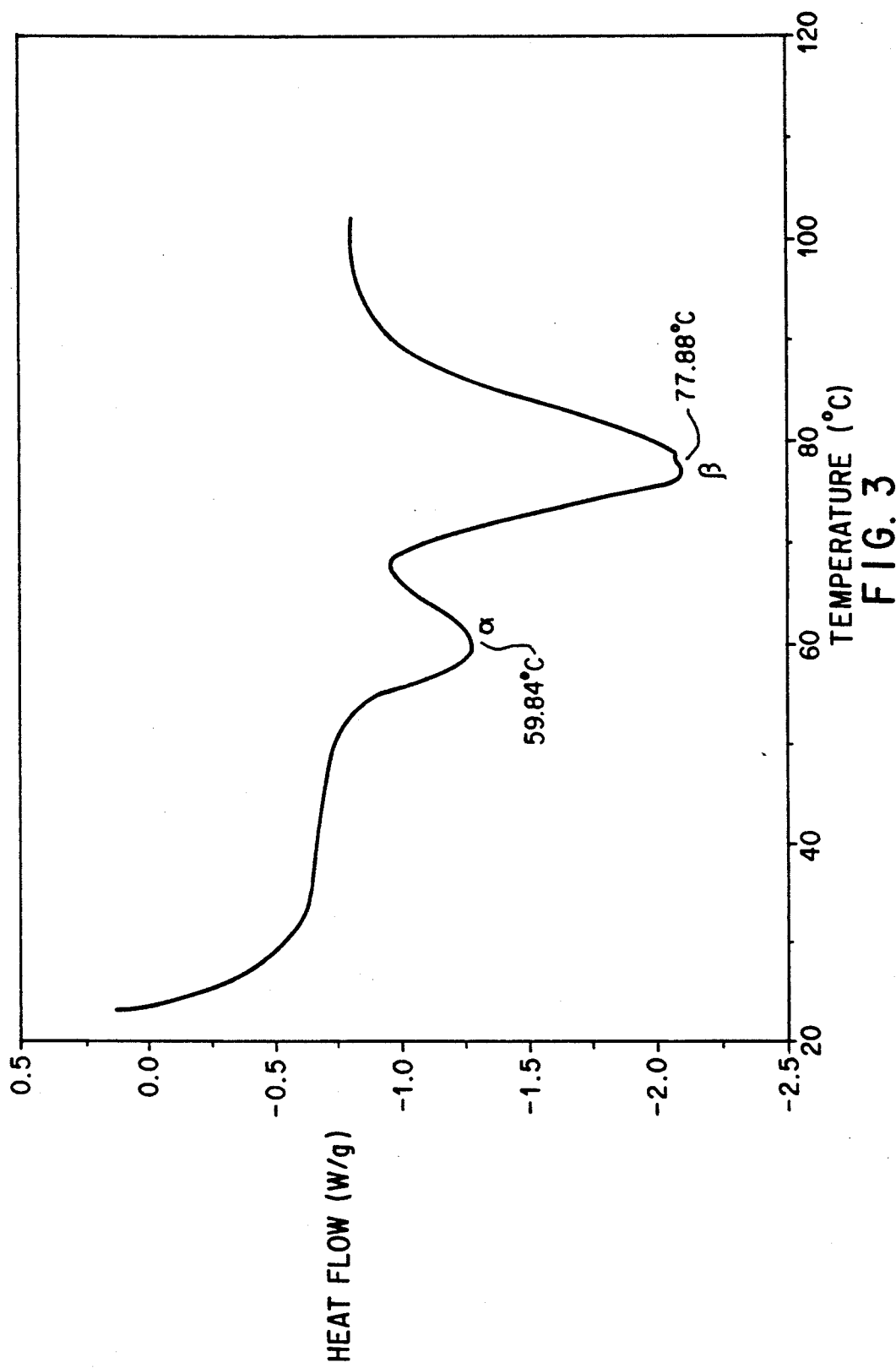
FIG. 3 is a DSC spectrum of glyceryl tristerate which has been melted to 90° C., subjected to the force of one piston stroke cycle, and resolidified.

FIG. 3 is the DSC spectrum of solidified tristearin which, while in the molten phase at 90° C., was subjected to the force of a single compression/expansion cycle of a piston stroke before solidification. Peaks corresponding to the polymorphic $\alpha$ and $\beta$ forms of the tristearin are still evident and are identified by appropriate legends in the Figure. The lower melting point polymorphic $\alpha$ form shows a peak centered at approximately 60° C. while the higher melting point polymorphic $\beta$ form shows a peak centered at approximately 78° C. The piston applied a maximum pressure to the wax of approximately 4400 pounds/inch$^2$ during the stroke cycle.

Figure 4:
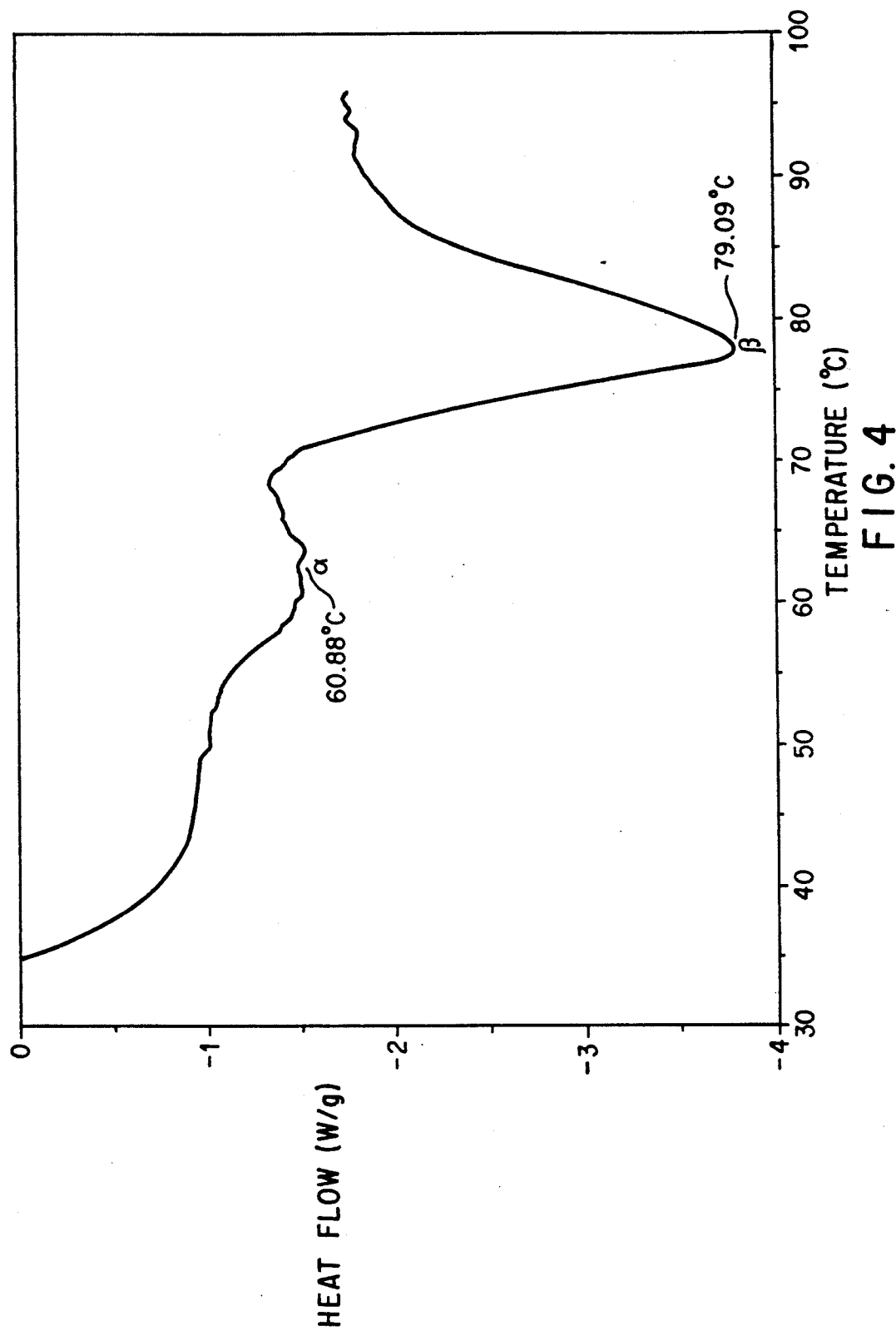
FIG. 4 is a DSC spectrum of glyceryl tristerate which has been melted to 90° C., subjected to the force of five piston stroke cycles, and resolidified.

FIG. 4 is a DSC spectrum of solidified tristearin which, while in the molten phase at 90° C., was subjected to the force of five compression/expansion cycles of a piston stroke before solidification. It can clearly be seen that a significantly smaller percentage of the material solidified material in the polymorphic $\alpha$ form than in the polymorphic $\beta$ form when compared to the material subjected to the force of a single stroke cycle of FIG. 3. The additional force applied by the piston stroke cycles to the material of FIG. 4 clearly transformed the molten phase of the wax to a state which solidified a larger percentage of its mass in the polymorphic $\beta$ form. In FIG. 4 the lower melting point polymorphic $\alpha$ form has a peak centered at approximately 61° C., while the higher melting point polymorphic β form has a peak centered at approximately 79° C. The piston applied a maximum pressure to the wax of approximately 4400 pounds/inch$^2$ during the stroke cycles.

Figure 5:
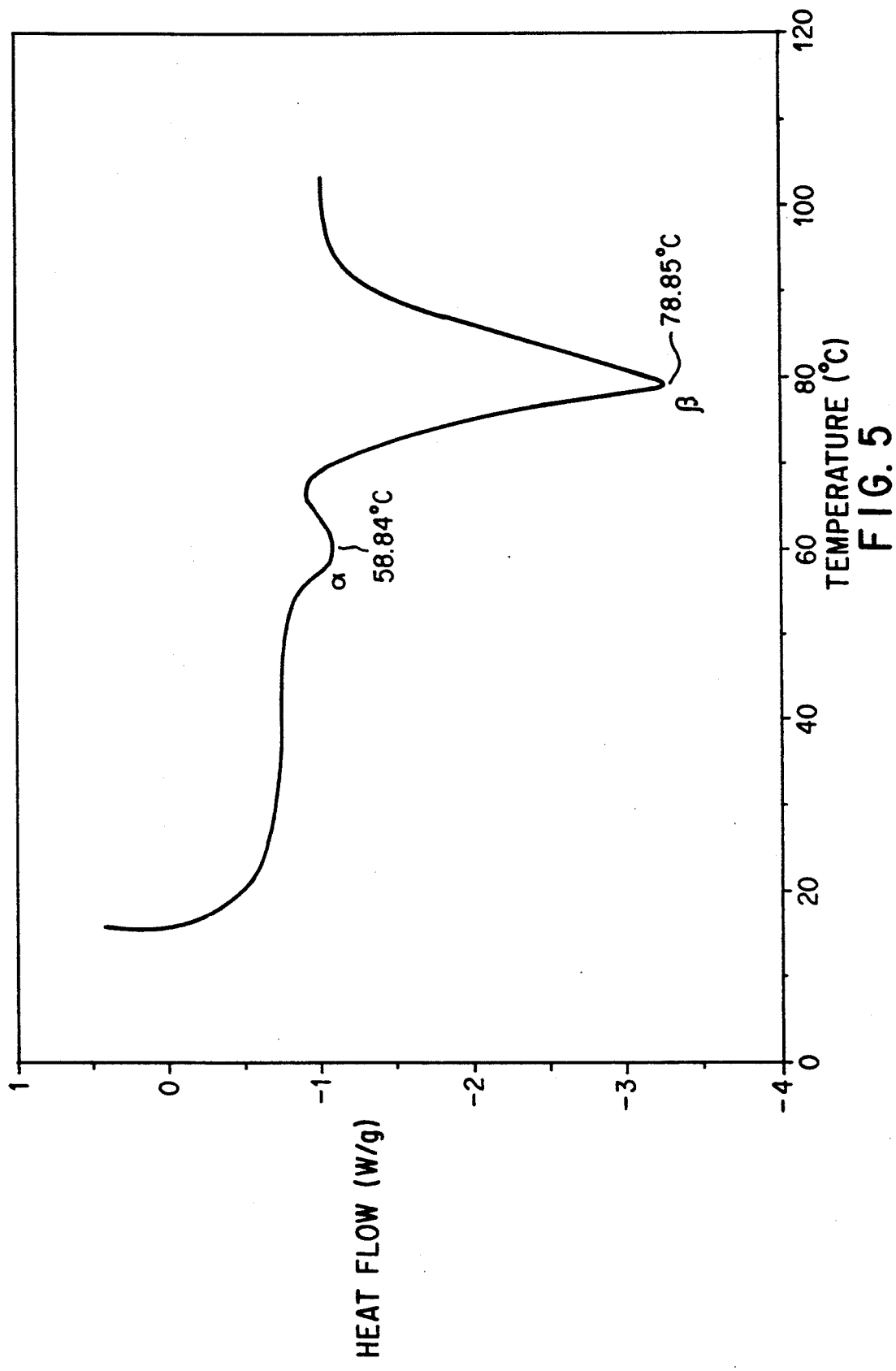
FIG. 5 is a DSC spectrum of glyceryl tristerate which has been melted to 90° C., subjected to the force of twenty piston stroke cycles, and resolidified.

FIG. 5 is a DSC spectrum of solidified tristearin which, while in the molten phase at 90° C., was subjected to the force of twenty compression/expansion cycles of a piston stroke before solidification. For this sample, the lower melting point polymorphic α form shows a peak centered at approximately 59° C., while the higher melting point polymorphic β form has a peak centered at approximately 79° C. Comparison of the ratios of the peak heights of FIG. 4 and FIG. 5 suggests that not much more of the molten wax was transformed into a state which would crystallize in the β polymorphic form by twenty stroke cycles than was accomplished by five stroke cycles of the piston. The piston applied a maximum pressure to the wax of approximately 4400 pounds/inch$^2$ during the stroke cycles.

However, it is quite evident when either the DSC spectra of FIG. 4 or FIG. 5 is compared to the DSC spectra of FIG. 3 that the force provided by additional piston stroke cycles transforms a larger fraction of the molten wax to a state which will solidify as the β polymorph than will solidify as the α polymorph.

Figure 6:
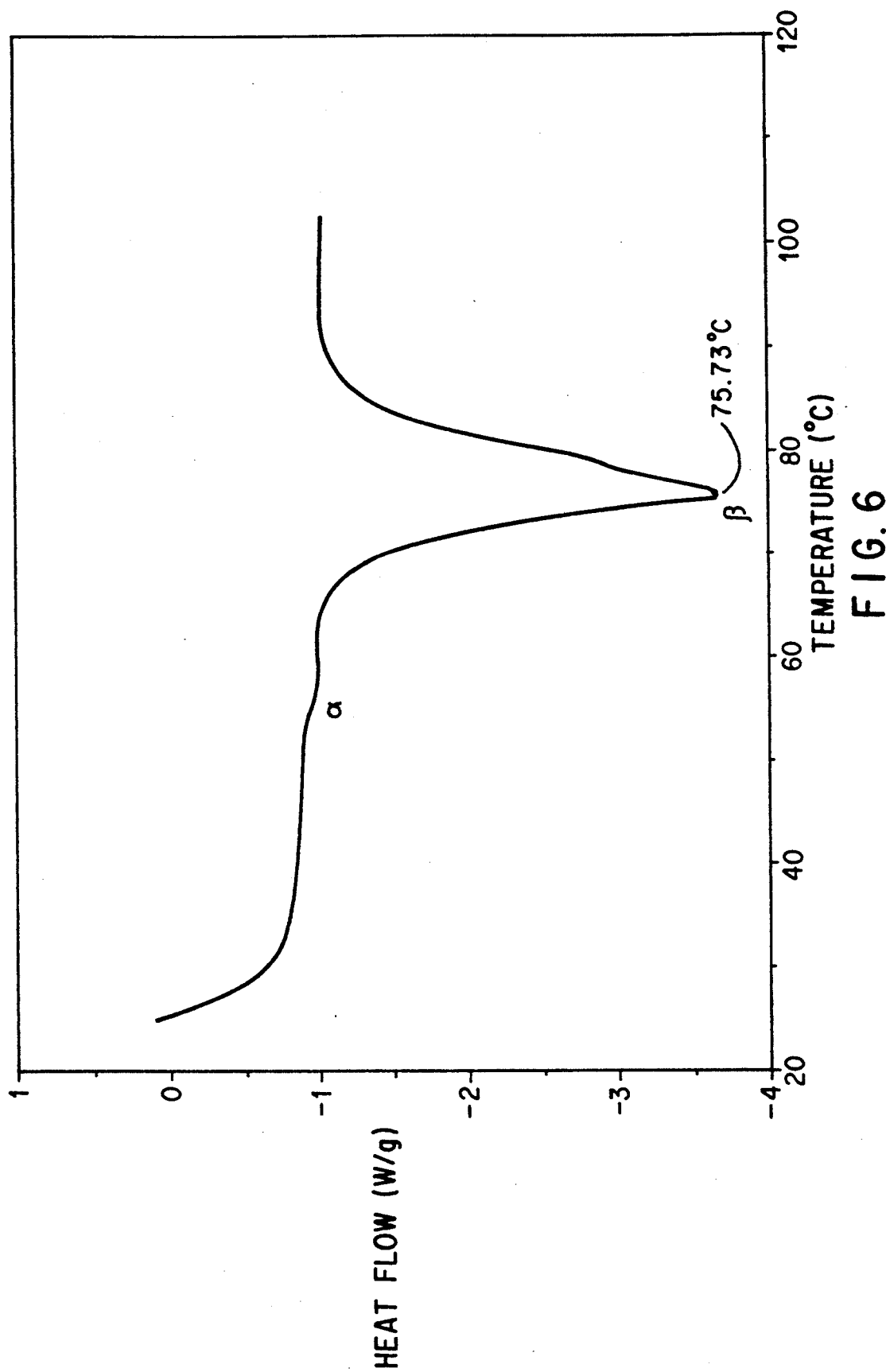
FIG. 6 is a DSC spectrum of glyceryl tristerate which has been melted to 145° C., subjected to the force of one piston stroke cycle, and resolidified.

FIG. 6 is the DSC spectrum of solidified tristearin which, while in the molten phase at 145° C., was subjected to the force of one compression/expansion cycle of the piston stroke before solidification. The very small endothermic peak centered at approximately 60° C. suggests that some residual polymorphic α form is still present. However, the relative magnitude of the larger polymorphic β peak centered at approximately 76° C. demonstrates that the transformed tristearin has solidified predominantly in the polymorphic β form. The piston applied a pressure to the wax of about 4400 pounds/inch$^2$ during the stroke cycle. The application of force clearly transformed the tristearin wax.

Figure 7:
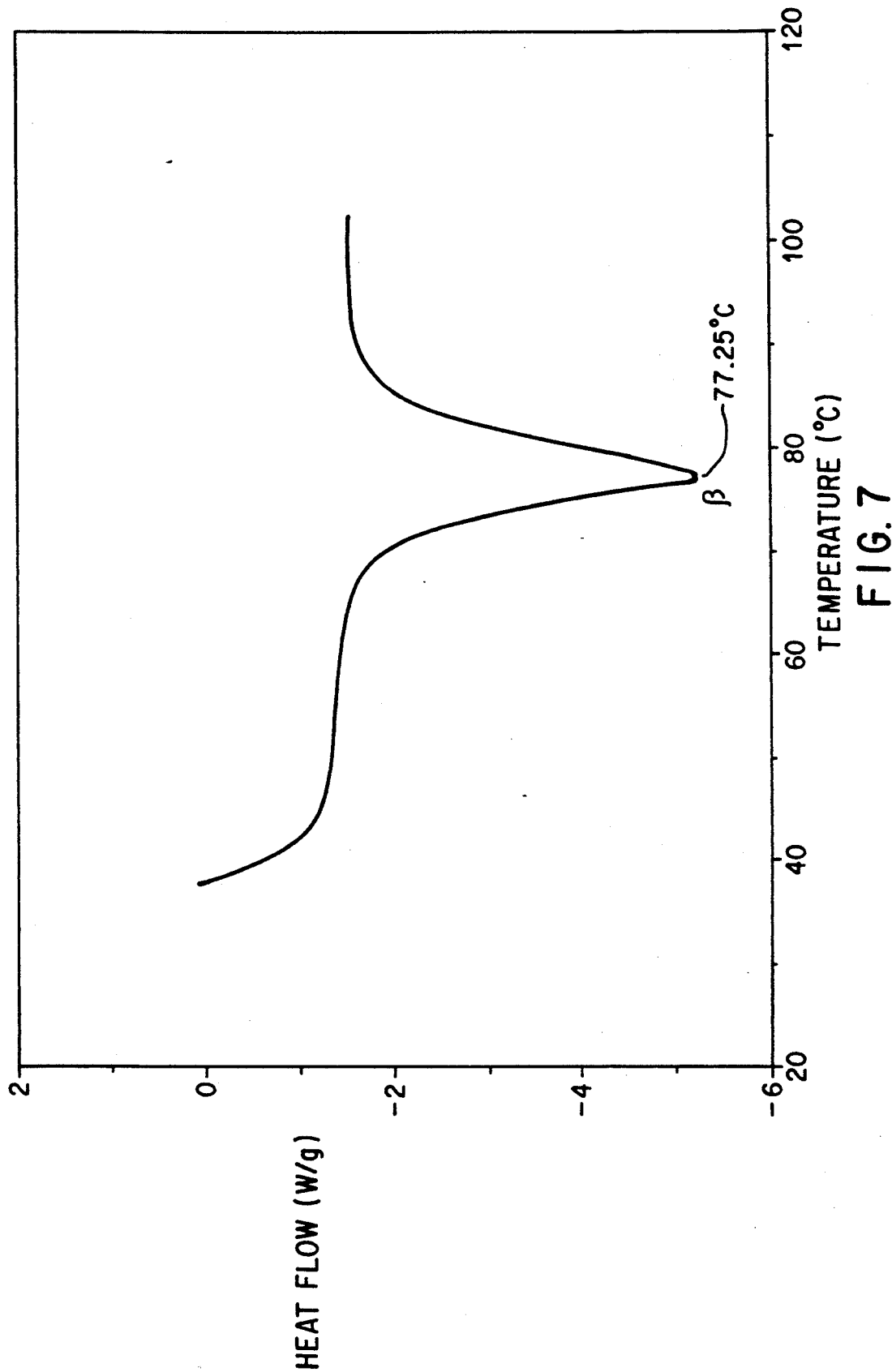
FIG. 7 is a DSC spectrum of glyceryl tristerate which has been melted to 145° C., subjected to the force of five piston stroke cycles, and resolidified.

FIG. 7 is the DSC spectrum of solidified tristearin which, while in the molten phase at 145° C., was subjected to the force of five compression/expansion cycles of a piston stroke before solidification. The presence of a single peak centered at approximately 77° C. clearly shows that the transformed tristearin has solidified in only the polymorphic β form. There is no indication of any residual polymorphic α form present. The piston applied a pressure to the wax of about 5500 pounds/inch$^2$ during each stroke cycle. In this case, the application of force has completely transformed a wax material, tristearin, which normally upon resolidification would crystallize in both the polymorphic α and β forms, to a state which upon resolidification now crystallizes in only the higher melting point polymorphic β form. This result is totally unexpected and unanticipated in the prior art.

Figure 8:
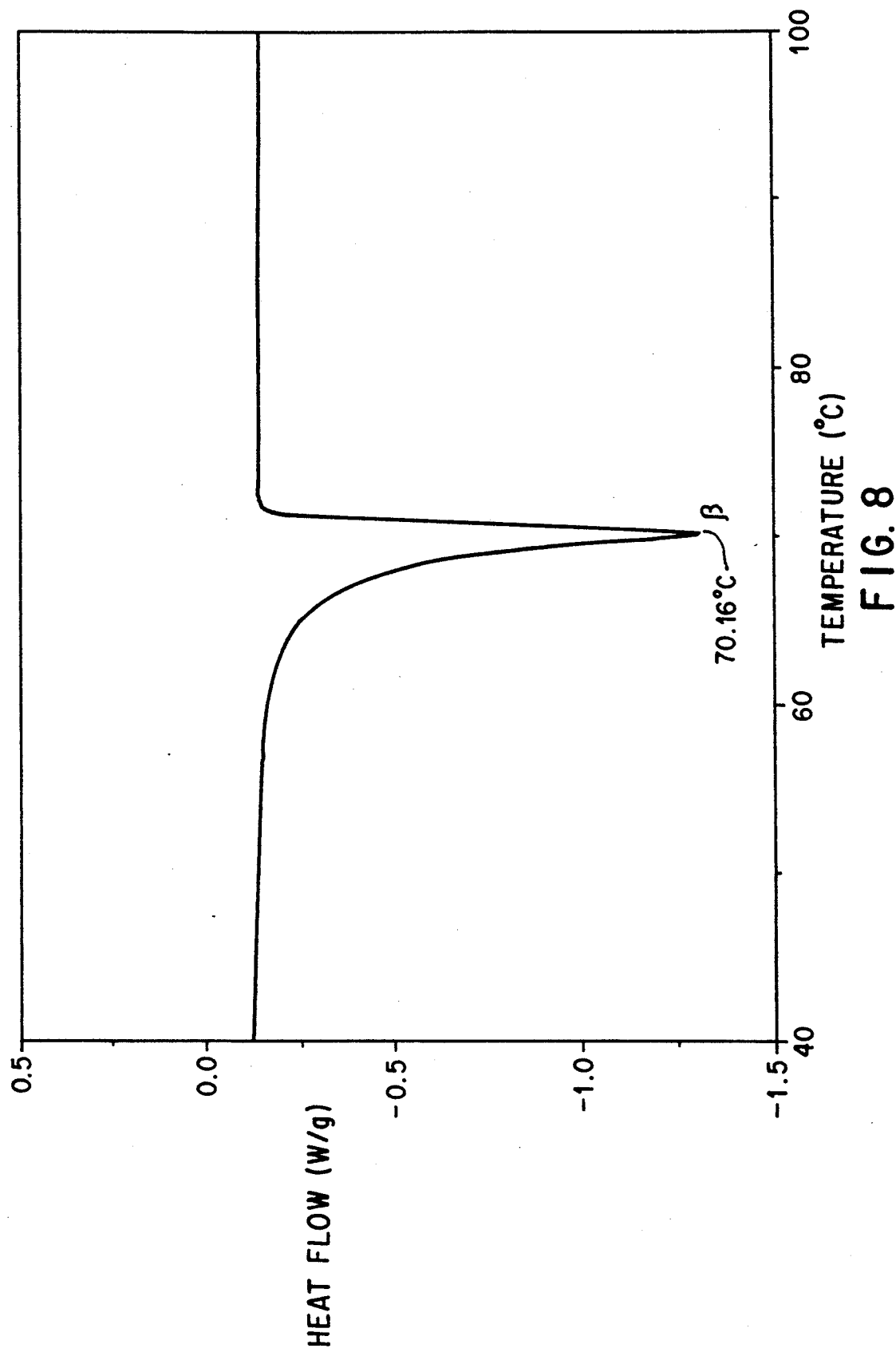
FIG. 8 is a DSC spectrum of glyceryl tristerate which has been melted to 120° C., subjected to the force of one piston stroke cycle, and resolidified.

FIG. 8 is the DSC spectrum of solidified tristearin which, while in the molten phase at 120° C., was subjected to the force of one compression/expansion cycle of a piston stroke before solidification. The piston applied a maximum pressure to the wax of approximately 9360 pounds/inch$^2$ during its stroke cycle In FIG. 8 the peak centered at approximately 70° C. corresponds to the polymorphic β form. FIG. 8 clearly demonstrates that transformation of the melted wax to a state which solidifies only in the higher melting point β polymorph can be achieved with a the force applied by a single stroke cycle of the piston. The transformation of the wax seems to depend on two factors: 1) the temperature of the liquid wax when force is applied; and 2) the total force applied to the molten wax.

Figure 9:
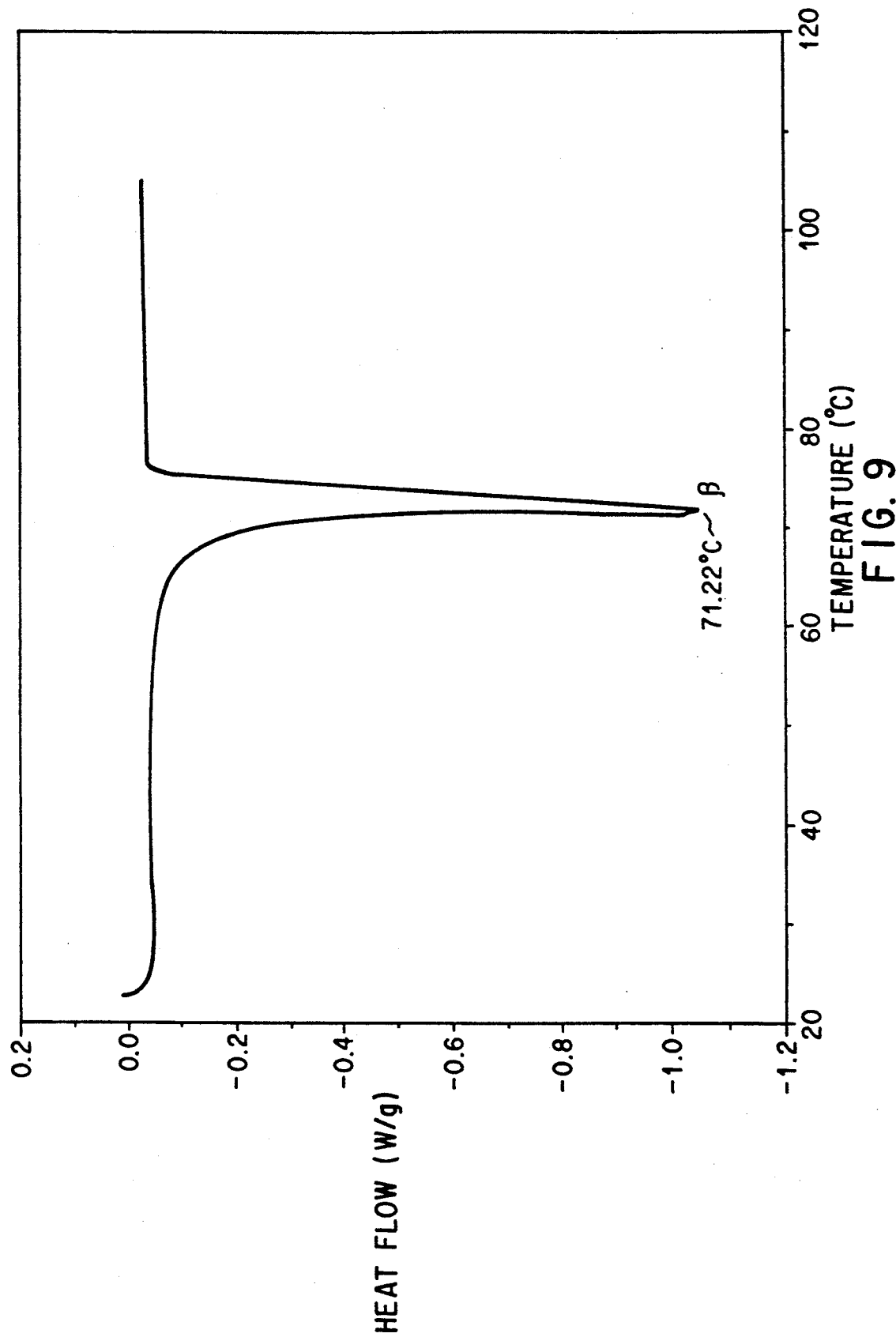
FIG. 9 is a DSC spectrum of glyceryl tristerate which has been melted, subjected to the force of ultrasound, and resolidified.

FIG. 9 is a DSC spectrum of solidified ultrasonically transformed tristearin. The tristearin was melted, heated to 90° C., and subjected for a period of ten minutes, while being stirred, to the force of ultrasound at an intensity level of 25 watts/cm$^2$. As can be seen from FIG. 9, upon resolidification, the ultrasonically transformed tristearin wax hardened entirely in the polymorphic β form yielding the customary β form peak centered at approximately 71° C. However, it should be noted that the time needed to transform the tristearin wax to the all β form by means of piston stroke cycles required only a few seconds, while the ultrasonic transformation required ten minutes. However, it is possible that either a greater total force applied by a higher power ultrasonic transducer or a different transducer geometry, cavity shape, or exposure area (such as in a flow cell) may effect the transformation in less time that the device presently available to Applicant.

In the above examples, a force applied to the molten wax transformed the wax to a different state. An example of an apparatus for producing the transforming force is shown schematically in FIG. 10. The apparatus, illustrated in FIG. 10, consists of a reservoir 1 having a stirrer 11 located so as to stir the wax contents 3 of reservoir 1. Reservoir 1 is heated, if necessary, by heating coils 2, and the temperature of the wax material 3 within reservoir 1 is determined by temperature measuring apparatus 18. A transfer conduit 14 leads to piston assembly 13. Piston assembly 13 consists of chamber 15, having inlet valve 6 and outlet valve 7 at opposite ends, to which is connected piston housing 4 which has within it movable piston 5. Movable piston 5 is displaced within housing 4 by motor 16. Motor 16 may be hydraulic, air, or electrically powered. Valves 6 and 7 may be solenoid valves, manually operated valves, or automatic check valves. Output transfer conduit 17 is connected to piston assembly 13 at exit valve 7 and leads to either a mixing or storage container (not shown). Transfer conduit 14 leading to piston assembly 13, piston chamber 15, and transfer conduit 17 leading from piston assembly 13 may be heated, if necessary, with heating coil 12 to maintain the temperature of the wax material 3 as it passes to, through, and from piston assembly 13. The mixing or storage containers (not shown) may be heated, if necessary, to maintain the temperature of the transformed wax material.

To prepare waxes for transformation, the native wax is first placed in reservoir 1 where, if necessary, it is melted and maintained above its melting point. Alternatively, previously melted or liquid wax (which exists in the liquid phase at ambient temperature) may be placed in reservoir 1. The liquid wax is stirred by stirrer 11 until it has a uniform temperature as determined by temperature measuring apparatus 18. In the preferred embodiment, reservoir 1 is located above piston assembly 13 so that liquid wax 3 is gravitationally fed to piston assembly 13. Liquid wax 3 is admitted to chamber 15 where, after the valves seal off chamber 15, it is subjected to force as piston 5 is driven by motor 16 through its positive and negative displacement cycle within housing 4. The liquid wax 3 is shown under pressure in chamber 15 as wax 8. After admitting liquid wax 3, valves 6 and 7 may be closed while the piston cycles, subjecting the liquid wax to force by alternately applying and relieving pressure on the wax within closed chamber 15. Alternatively, the valve action may be adjusted to provide a semi-continuous flow of liquid wax through chamber 15. This can be accomplished by using check valves for both inlet valve 6 and outlet valve 7. As the piston is raised, the pressure within chamber 15 drops below the outside ambient pressure. Check valve 7 prevents previously transformed material from reentering chamber 15 while check valve 6 permits a quantity of liquid wax 3 to be drawn into chamber 15. As piston 5 begins the downward half of its stroke cycle, both check valves 6 and 7 close for a period of time allowing pressure to build up within chamber 15. At some point the pressure on liquid wax 3 exceeds the pressure setting of check valve 7 which then opens, permitting the transformed wax to flow out of chamber 15 into transfer conduit 17.

As shown earlier with reference to FIG. 7, complete transformation of molten tristearin at 145° C. to a liquid state which will solidify substantially in the all $\beta$ polymorphic form is achieved after five repetitive stroke cycles of piston 5, each compression yielding approximately 5500 pounds/in$^2$ chamber pressure. Typically, only a couple of seconds are required to transform the wax material in this manner. Thus, the throughput of transformed wax is very high even for a small chamber. In the preferred embodiment of the piston apparatus, piston assembly 13 consists of an air driven hydraulic pump such as that manufactured by S. C. Hydraulic Engineering Corporation, Model No. SC-10-600-8. In such a pump, the force exerted by the piston on the liquid wax material within the chamber can be regulated by the choice of air pressure supplied to the motor. For the Model SC-600-8 pump, a minimum of approximately 35 pounds/inch$^2$ inlet pressure is required to activate the pump. Typical inlet pressure ranges to the pump which were found to produce sufficient force vary from 40 to 60 pounds/inch$^2$ of pressure. These inlet pressures result in pressures in the chamber of approximately 4400 to 6600 pounds/inch$^2$ since the pump has a hydraulic pressure multiplying effect of approximately 110. Chamber pressures as high as approximately 9360 pounds/inch$^2$ have been used with other pumps to successfully transform the waxes.

The transformed wax material 19 may either be collected for later use in a storage container heated, if necessary, to keep the material in the liquid phase or may be immediately used.

Figure 11:
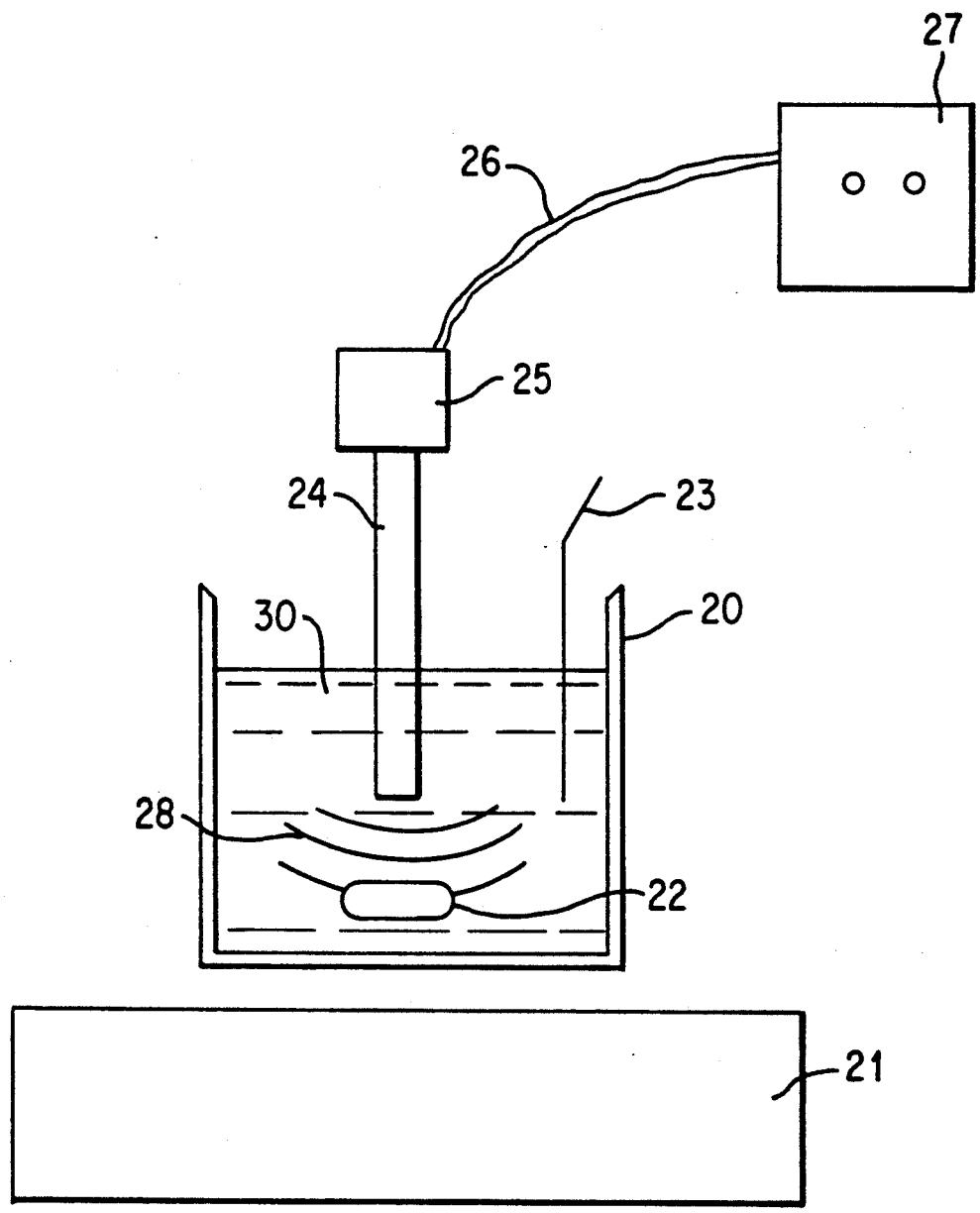
FIG. 11 is a schematic representation of an ultrasonic apparatus which produces the force necessary to transform waxes.

An example of a second apparatus for producing the transforming force is shown in FIG. 11. A treatment container 20 may be heated, if necessary, by heater/stirrer 21 which is a combination heating element and magnetic stirrer. The native wax 30 which is to be transformed, in either liquid or solid phase is placed in container 20. If necessary, wax 30 may be heated by heater/stirrer 21 while being stirred by magnetic bar stirrer 22 driven by heater/stirrer 21 and brought to a uniform temperature as determined by temperature measuring apparatus 23. After the wax 30 has reached the desired uniform temperature, horn 24 of ultasonic converter 25 is placed into the liquid wax 30. Converter 25 is connected by cable 26 to ultrasonic generator power supply 27. Ultrasound 28 is applied to liquid wax 30, once again resulting in transformation of liquid wax 30 into a liquid state of the wax which solidifies to a physically distinguishable form. For tristearin, a temperature of 90° to 145° C. is used. Typically, molten tristearin is subjected to the force of the ultrasound for a period of ten minutes at an intensity level of 25 watts/cm$^2$. Stirring is continued during the application of the ultrasound to ensure exposure of all the molten tristearin to the ultrasound. Once the transformation is complete, the transformed molten tristearin may be stored in a heated container or used immediately.

Figure 10:
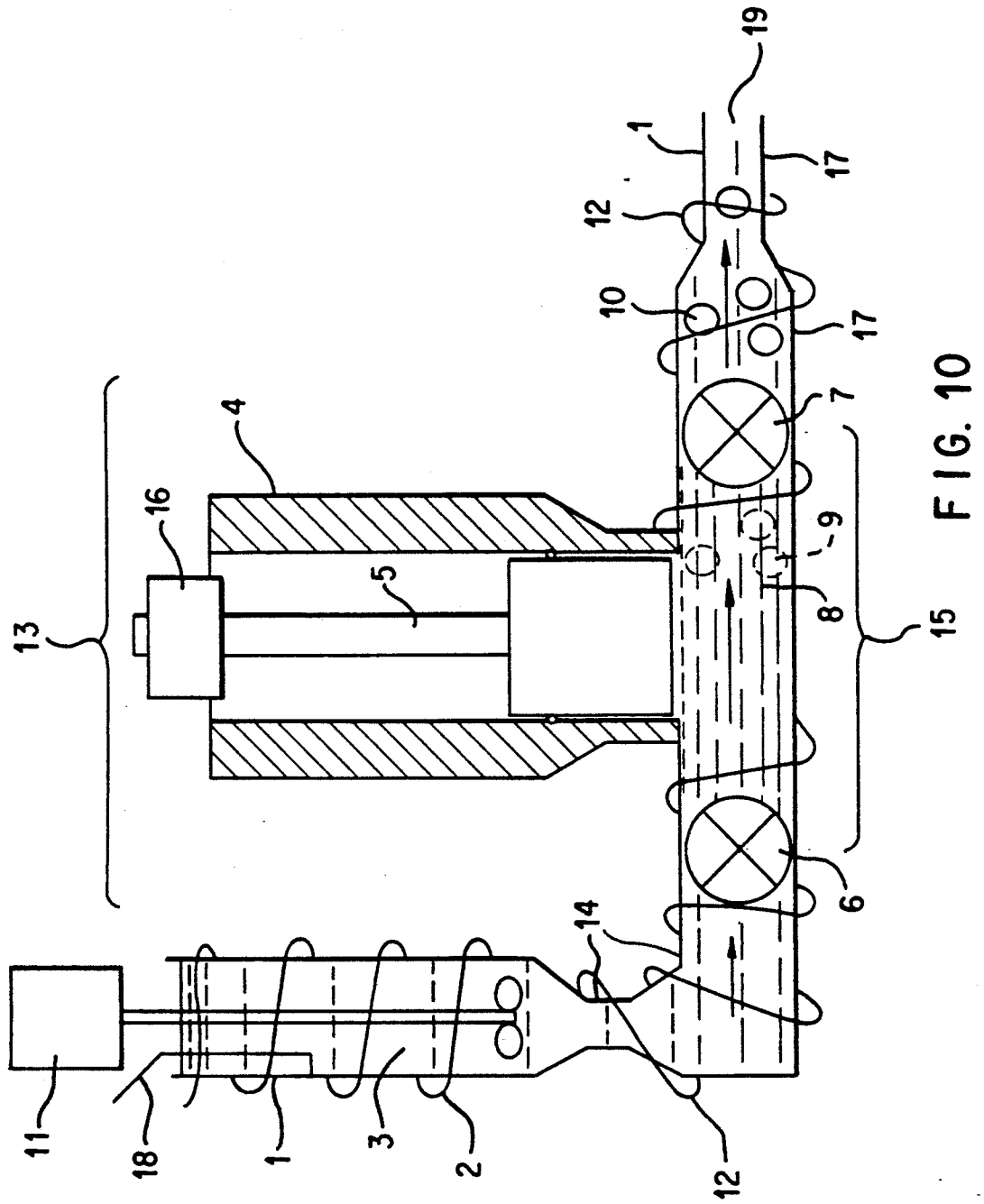
FIG. 10 is a schematic representation of a piston apparatus which produces the force necessary to transform waxes.

Several possible physical mechanisms may account for the transformation of the waxes by the applied force. For those polymorphic waxes, such as tristearin, which convert to a molten state which hardens in the stable higher melting point $\beta$ polymorph, a possible mechanism may be that at the high pressure achieved as the piston is forced against the molten wax within chamber 15, the molten wax begins to crystallize in the $\beta$ form. These initial $\beta$ form crystals 9 are indicated in FIG. 10 within a pressurized liquid wax 8. Upon leaving chamber 15 the $\beta$ form crystals 10 would serve as nucleation centers for further ordering of the molecules so that, as the wax solidified, it would crystallize principally in the polymorphic $\beta$ form. By this mechanism, more $\beta$ form crystals 10 are created by each successive application of force by the piston stroke cycles, thereby creating a larger number of $\beta$ form nucleation centers. At some point the concentration of $\beta$ form nucleation centers 10 would be sufficient to cause the solidification of the liquid wax completely in the polymorphic $\beta$ form. Applicant, however, does not rule out as a possible mechanism the alternative possibility that it is the release of pressure either during the piston's negative displacement or by release of the pressurized wax through the check valve which initiates $\beta$ form crystal formation.

On the other hand, the force may work through means other than pressure to transform the waxes. That some other mechanism is at work is suggested by the fact that the force generated by ultrasound also transforms the molten waxes. Ultrasound is usually considered to work its effects through the creation of cavitation bubbles in the medium, although pre-cavitation oscillation of the medium occurs. The collapse of cavitation bubbles is accompanied by localized shock waves, shear forces, and abrupt temperature spikes. Perhaps it is the force applied by shear, shock wave, or heating produced by either the piston cycle or ultrasound that transforms the waxes. Applicant has discovered the effect but does not know the mechanism.

One important use for the transformed waxes is as shell material for encapsulation of environmentally sensitive materials, particularly hygroscopic and deliquescent materials for which protection from ambient moisture is important. The use of the transformed waxes to encapsulate core materials is more fully discussed in co-pending U.S. patent application entitled "Encapsulation of Environmentally Sensitive Materials" filed on even date herewith.

Figure 12:
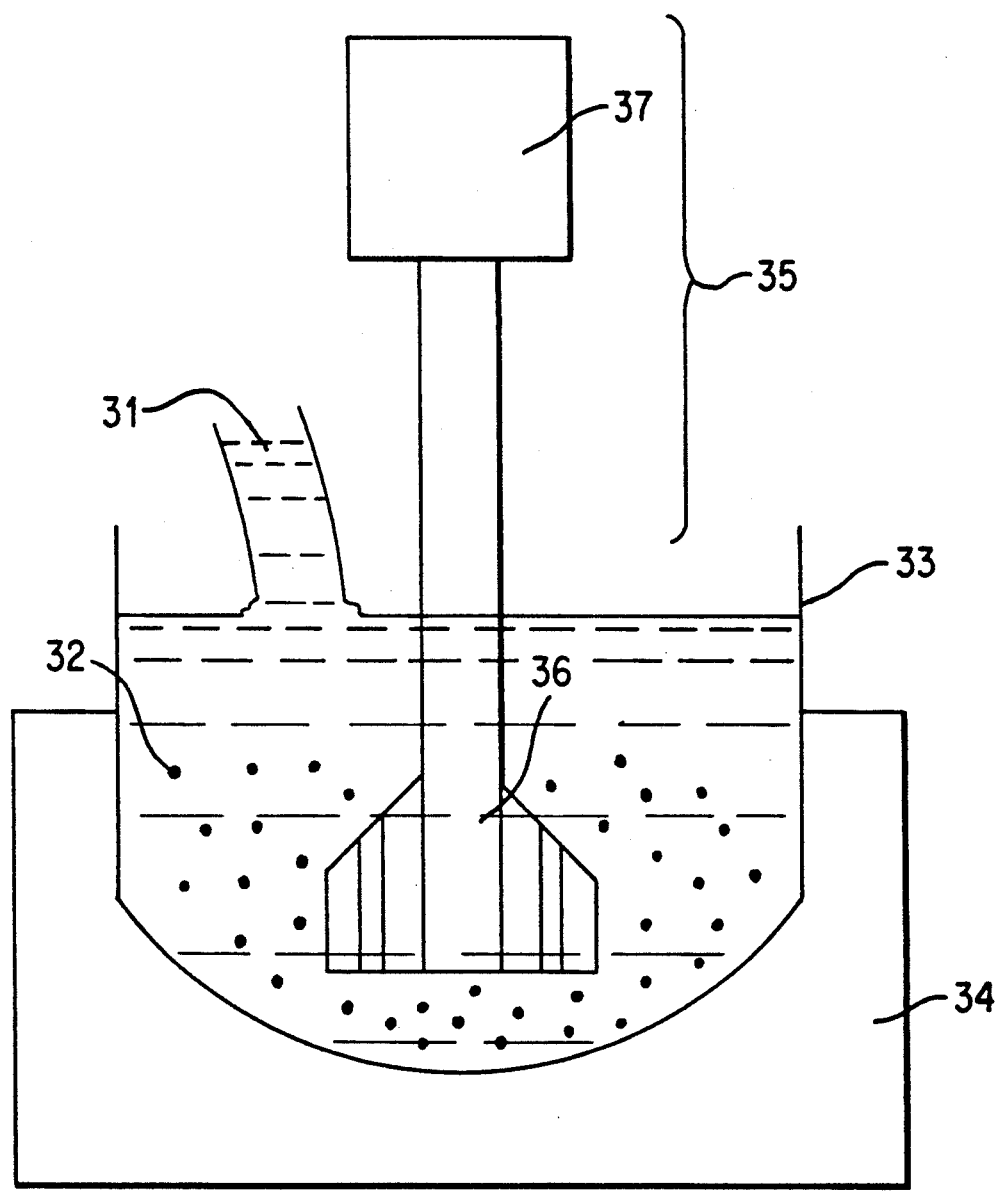
FIG. 12 is a schematic representation of an apparatus used to encapsulate core materials with transformed wax.

FIG. 12 shows the apparatus used to encapsulate core materials with wax transformed by the method and apparatus of this invention. Liquid wax 31 transformed by being subjected to force is added along with core material 32 to mixing container 33. Mixing container 33 may be heated if necessary to maintain the wax in the liquid phase by a heating mantle or jacket 34. The core material 32 and transformed wax shell material 31 are mixed by mixer/stirrer 35. Mixer/stirrer 35 provides mechanical agitation to the mixture of core material 32 and transformed shell material 31 to ensure complete coating/encapsulation of the core material 32.

Mixer/stirrer paddle 36 is powered by motor 37 which in the preferred embodiment provides both a rotating and reciprocating action to stirrer paddle 36. Transformed wax shell material 31 solidifies around core material 32 after the heat to container 33 is removed. Alternatively, the heat supplied by heater 34 to container 33 may be gradually reduced during mixing. Once solidified, the transformed wax creates a permanent coating or shell about the core material particle, forming a capsule.

The particle size of the initial core material 32 will basically determine the size of the resulting capsule. Depending upon the size of the starting core material, the resultant capsule may be classified as either a microcapsule or a macrocapsule recognizing that these terms are imprecise. For waxes which must be heated to a liquid phase, the encapsulation process can be accelerated to some extent by chilling container 33 during agitation of the core and shell mixture. However, best results are obtained by cooling the core and shell mixture slowly while continuing the mixing agitation. To facilitate encapsulation, the core material may also be preheated to a temperature below that of the liquid transformed wax shell material before mixing with the transformed wax shell material.

Choline chloride is an example of an extremely hygroscopic compound successfully encapsulated using the above method with transformed waxes. Using choline chloride as the core material and transformed molten tristearin as the shell material, capsules of choline chloride are obtained having stable shell walls which do not degrade over time. The choline chloride capsules which yields the superior shell and offers the best protection for the core material.

When used as a shell material in an encapsulation process, liquid wax transformed by the method and apparatus of this invention produces capsule shells which are more resistant to environmental conditions and which, therefore, protect more fully the core materials from environmental influences. The use of transformed tristearin as shell wall material about a core of choline chloride is a good example. Such capsules do exhibit a gain in weight over a period of time upon continuous exposure to humid atmospheric conditions. This gain in weight is attributed to either water adsorption onto the capsules or water absorption by the capsules.

To measure the relative weight gain over time, comparison is made to choline bitartrate which has been coated with silicon dioxide particles. Since choline bitartrate is much less hygroscopic than choline chloride, it is frequently used where choline must be compounded. However, the higher molecular weight of the choline bitartrate makes it unsuitable for many applications where choline is needed. Table 2 illustrates the percentage weight gains seen for four samples: untreated choline chloride, choline bitartrate, choline chloride coated with nontransformed native tristearin, and choline chloride coated with transformed tristearin.

TABLE 2

COMPARISON OF MOISTURE ABSORPTION OF ENCAPSULATED CHOLINE CHLORIDE VS. UNTREATED ADSORPTION CONTROL SAMPLES

| SAMPLE MATERIAL | WEIGHT GAIN OVER 3 HOURS 100% HUMIDITY | WEIGHT GAIN OVER 6 HOURS 100% HUMIDITY | QUANTITY OF CHOLINE PRESENT IN SAMPLE |
|---|---|---|---|
| CHOLINE CHLORIDE UNTREATED | 21.7% | 36.2% | 85% |
| CHOLINE BITARTRATE $SiO_2$ | 8.0% | 13.2% | 47% |
| ENCAPSULATED CHOLINE CHLORIDE IN DYNASAN −118; NATIVE 70:30 CORE/SHELL | 20.8% | 35.0% | 59.5% |
| ENCAPSULATED CHOLINE CHLORIDE IN DYNASAN −118; TRANSFORMED 70:30 CORE/SHELL | 18.3% | 29.5% | 59.5% |

(averages over 5 samples - absolute weight increases by %)

are also free-flowing; that is, no clumping or agglutination of the capsules occurs, and they remain free to slide by one another. This makes such choline chloride capsules useful for forming into tablets by means well known in the art. Choline chloride capsules formed with transformed tristearin shells appear in micrographs to have a complete and unbroken shell.

The polymorphic form of the native tristearin wax represented by the re-solidified sample of FIG. 2 does not form a suitable shell for the protection of environmentally sensitive materials. When used to coat or encapsulate a core material, the polymorphic form allows greater access to the core material by external conditions such as moisture, oxidizing or reducing substances, and other chemical reactants. Glyceryl tristearate which has been transformed by the method and apparatus of this invention so as to be converted to substantially all $\beta$ polymorphic form provides a more complete barrier against penetration to the core material by external conditions. Although core materials may be encapsulated with either the polymorphic or the transformed form of glyceryl tristearate, it is the transformed form It can be seen form Table 2 that choline chloride capsules made with native or transformed tristearin shells gain more weight than does the choline bitartrate but much less weight than the untreated choline chloride. The weight gained versus the actual amount of choline present in the samples shows a marked improvement for the transformed wax capsules over the native wax capsules and for the transformed wax capsules is almost equivalent to that for raw choline chloride. In these experiments, after six hours much of the untreated choline chloride deliquesces leaving some remaining material resting in a small pool of liquid. Similarly, after six hours the native wax capsules had moisture droplets or beads on their surface. However, after six hours the transformed wax capsules remained visibly dry and free flowing. Thus, the principal problem with working with choline chloride, that of its hygroscopicity, has been overcome by encapsulation in the transformed wax shell.

Clearly, shells formed from native tristearin are not as effective in preventing weight gain as are shells formed from transformed tristearin. This is believed to be due to the presence of multiple polymorphic states in the native material which degrade the structural integrity of the shell.

The choline chloride capsules formed with transformed tristearin remain free-flowing even after exposure to a 100% humidity environment with its accompanying weight gain, and microscopy shows no change in the structure of the shell. Furthermore, after extended exposure to humid atmospheric conditions, analysis of the choline content of the transformed tristearin choline chloride capsules indicates that the choline which was originally encapsulated remains within the capsule and active.

As mentioned, the reasons for the weight gain are not entirely clear. It is possible that some water may be absorbed into the shell layer interstitially between the waxy tristearin molecules. It is also possible that some of the water reaches the choline chloride core of the capsules. Another possibility is that water adheres to the surface of the capsules, and, finally, it is possible that some residual choline which was not encapsulated during the mixing adheres to the surface of the capsules and may be absorbing the water. However, micrographs show no indication of such residual choline chloride crystals on the outside surface of the capsule shells. Whatever the reasons for the weight gain, capsules of choline chloride core in a transformed tristearin shell remain free-flowing and retain the choline within the capsules without leaking. The transformed tristearin wax is clearly a superior shell material.

While the method and apparatus of this invention have been discussed using as an example, glyceryl tristearate, it is clear that the invention is not limited to waxes which are normally solid at room temperature and which are useful for encapsulation. The method and apparatus of this invention may be used with waxes which are liquid at ambient temperatures and which are then used in the transformed state for purposes other than encapsulation. Clearly, Applicant has discovered that the waxes, after being subjected to force, exist in a transformed liquid state having properties significantly different from those possessed before being subjected to the force. The transformed waxes of this invention may significantly change the manner and uses to which waxes are put in a wide variety of commercial processes. The transformed waxes may be put to such uses both in the solidified and liquid state after transformation. While Applicant has disclosed two alternative apparatuses for subjecting the waxes to force, Applicant's discovery is clearly not limited to the two apparatuses described. The extent of Applicant's invention shall only be circumscribed by the following claims.

What is claimed is:

1. A method for transforming a polymorphic wax from its alpha to its beta form comprising the following steps:
   a. melting the wax;
   b. placing and confining the wax in a chamber wherein it may be subjected to the action of a piston;
   c. subjecting the wax in the chamber to at least one stroke of the piston prior to solidification; and
   d. permitting the wax to solidify.

2. A method for transforming a polymorphic wax from its alpha to its beta form comprising the following steps:
   a. melting the wax;
   b. subjecting the wax to ultrasound prior to solidification; and
   c. permitting the wax to solidify.

3. A method for transforming a polymorphic wax from its alpha to its beta form comprising melting the wax, subjecting the wax in its molten state to a force prior to solidification, and permitting it to solidify.

4. The method of claim 3 wherein the wax is subjected to a force by:
   a. placing and confining the molten wax in a chamber wherein it may be subjected to the action of a piston; and
   b. subjecting the molten wax in the chamber to at least one stroke of the piston.

5. The method of claim 3 wherein the molten wax is subjected to a force by subjecting it to ultrasound.

6. A method for transforming a polymorphic wax from its alpha form to the stable higher melting point beta form comprising:
   a. melting the wax;
   b. placing and confining the molten wax in a chamber wherein it may be subjected to the action of a piston;
   c. subjecting the molten wax in the chamber to at least one stroke of the piston prior to solidification; and
   d. permitting the wax to solidify.

7. A method for transforming a polymorphic wax from its alpha form to the stable higher melting point beta form comprising the following steps:
   a. melting the wax;
   b. subjecting the molten wax to ultrasound prior to solidification; and
   c. permitting the wax to solidify.

8. A method for transforming a polymorphic wax from its alpha to its beta state comprising melting the wax, subjecting the wax in its molten state to pressure prior to solidification, and permitting it to solidify.

9. The method of claim 8 wherein the molten wax is subjected to pressure by:
   a. placing and confining the molten wax in a chamber wherein it may be subjected to the action of a piston; and
   b. subjecting said wax in the chamber to at least one stroke of the piston.

10. The method of claim 8 wherein the molten wax is subjected to pressure by subjecting it to ultrasound.

11. A method for transforming a polymorphic wax from its alpha to its beta state comprising melting the wax, subjecting the wax in its molten state to a shock wave prior to solidification, and permitting it to solidify.

12. The method of claim 11 wherein the polymorphic wax is subjected to a shock wave by:
   a. placing and confining the molten wax in a chamber wherein it may be subjected to the action of a piston; and
   b. subjecting said wax in the chamber to at least one stroke of the piston.

13. The method of claim 11 wherein the molten wax is subjected to a shock wave by subjecting the molten wax to ultrasound.

14. A method for transforming a polymorphic wax from its alpha to its beta form comprising melting the wax, subjecting the wax in its molten state to shear prior to solidification, and permitting it to solidify.

15. The method of claim 14 wherein the polymorphic wax is subjected to shear by:

a. placing and confining the molten wax in a chamber wherein it may be subjected to the action of a piston; and b. subjecting the molten wax in the chamber to at least one stroke of the piston.

16. The method of claim 14 wherein the polymorphic wax is subjected to shear by subjecting the molten wax to ultrasound and permitting it to solidify.

17. A method for transforming a polymorphic wax from its alpha to its beta form comprising melting the wax, subjecting the wax in its molten state to an abrupt pressure change prior to solidification and permitting it to solidify.

18. The method of claim 17 wherein the polymorphic wax is subjected to an abrupt pressure change by:

a. placing and confining the molten wax in a chamber wherein it may be subjected to the action of a piston; and b. subjecting the wax in the chamber to at least one stroke of the piston.

19. The method of claim 17 wherein the polymorphic wax is subjected to an abrupt pressure change by subjecting the molten wax to ultrasound.

20. The method of claim 1, wherein the wax is a triglyceride.

21. The method of claim 2 wherein the wax is a triglyceride.

22. The method of claim 3 wherein the wax is a triglyceride.

23. The method of claim 4 wherein the wax is a triglyceride.

24. The method of claim 5 wherein the wax is a triglyceride.

25. The method of calming 6 wherein the wax is a triglyceride.

26. The method of claim 7 wherein the wax is a triglyceride.

27. The method of claim 8 wherein the wax is a triglyceride.

28. The method of claim 9 wherein the wax is a triglyceride.

29. The method of claim 10 wherein the wax is a triglyceride.

30. The method of claim 11 wherein the wax is a triglyceride.

31. The method of claim 12 wherein the wax is a triglyceride.

32. The method of claim 13 wherein the wax is a triglyceride.

33. The method of claim 14 wherein the wax is a triglyceride.

34. The method of claim 15 wherein the wax is a triglyceride.

35. The method of claim 16 wherein the wax is at triglyceride.

36. The method of claim 17 wherein the wax is a triglyceride.

37. The method of claim 18 wherein the wax is a triglyceride.

38. The method of claim 19 wherein the wax is a triglyceride.

* * * * *

UNITED STATES PATENT AND TRADEMARK OFFICE
CERTIFICATE OF CORRECTION

PATENT NO. : 5,209,879
DATED : May 11, 1993
INVENTOR(S) : Bruce K. Redding, Jr.

It is certified that error appears in the above-identified patent and that said Letters Patent is hereby corrected as shown below:

Column 2, line 28, the phrase "c form" should be replaced with the phrase --$a$ form--

Column 9, line 32, the word "SC-600-8" should be replaced with the phrase --SC-10-600-8--

Column 16, line 3, the word "calming" should be replaced with the word --claim--

Signed and Sealed this

Fifteenth Day of March, 1994

Attest:

BRUCE LEHMAN

*Attesting Officer*     *Commissioner of Patents and Trademarks*